(12) United States Patent
Castan et al.

(10) Patent No.: US 7,879,362 B2
(45) Date of Patent: Feb. 1, 2011

(54) ORAL PHARMACEUTICAL COMPOSITIONS WITH CONTROLLED RELEASE AND PROLONGED ABSORPTION

(75) Inventors: Catherine Castan, Orlienas (FR); Valerie Legrand, Lyons (FR); Rémi Meyrueix, Lyons (FR); Gérard Soula, Meyzieu (FR)

(73) Assignee: Flamel Technologies, Venissieux (FR)

( * ) Notice: Subject to any disclaimer, the term of this patent is extended or adjusted under 35 U.S.C. 154(b) by 0 days.

(21) Appl. No.: 11/723,553

(22) Filed: Mar. 21, 2007

(65) Prior Publication Data

US 2007/0207214 A1 Sep. 6, 2007

Related U.S. Application Data

(63) Continuation of application No. 10/332,463, filed on Jan. 9, 2003, now abandoned.

(51) Int. Cl.
*A61K 9/16* (2006.01)
(52) U.S. Cl. ............... 424/494; 424/400; 424/497; 424/489; 424/490; 424/493
(58) Field of Classification Search ............... 424/1.11, 424/1.21, 1.29, 1.25, 1.33, 1.1, 1.45, 1.49, 424/1.53, 1.65, 1.69, 1.73, 1.81, 9.7, 400, 424/450, 451, 489, 490, 491, 492, 493, 494, 424/495, 496, 497, 500, 501, 502, 452, 455, 424/456, 457, 458, 459, 460, 461, 462, 463, 424/464, 465
See application file for complete search history.

(56) References Cited

U.S. PATENT DOCUMENTS

| 5,268,182 | A |   | 12/1993 | Brinker et al. |
|---|---|---|---|---|
| 5,472,704 | A |   | 12/1995 | Santus et al. |
| 5,846,566 | A |   | 12/1998 | Burguiere et al. |
| 5,858,398 | A |   | 1/1999 | Cho |
| 5,945,123 | A | * | 8/1999 | Hermelin ............... 424/464 |
| 6,022,562 | A | * | 2/2000 | Autant et al. ............ 424/489 |
| 6,068,859 | A | * | 5/2000 | Curatolo et al. ......... 424/490 |
| 6,671,904 | B2 |   | 1/2004 | Easterling |

FOREIGN PATENT DOCUMENTS

| EP | 0 609 961 | 8/1994 |
|---|---|---|
| EP | 0 624 371 | 11/1994 |
| EP | 0 709 087 | 5/1996 |
| WO | WO 96/08243 A1 | 3/1996 |
| WO | WO 96/11675 | 4/1996 |
| WO | WO 99/47125 | 9/1999 |
| WO | WO 99/47128 | 9/1999 |

* cited by examiner

*Primary Examiner*—D L Jones
(74) *Attorney, Agent, or Firm*—Patton Boggs LLP

(57) ABSTRACT

The invention concerns a galenic system with prolonged/controlled release of the medicinal and/or nutritional active principle, for oral administration. The aim is to provide a system enabling to obtain with one single tolerable and acceptable dose of active principle, efficient therapeutic protection over 24 hours (increasing the bioabsorption time without affecting bioavailability). To achieve this, the invention provides a composition comprising two controlled release systems associated in series, namely: individualised coated particles (microcapsules) of active principle forming an internal phase, the coating comprising a film-forming polymer $P_1$ (ethylcellulose), a nitrogenous polymer (polyvinylpyrrolidone), a softener (castor oil) and a lubricant (magnesium stearate), and an external phase of functional carriers: polyelectrolytic hydrophilic polymer: (alginate), neutral hydrophilic polymer (hydroxypropylmethylcellulose) and a gelling additive (calcium acetate), said composition spontaneously forming in the presence of water, a cohesive and stable composite macroscopic solid, wherein the external continuous phase is a gelled matrix including the active principle microcapsules. The invention is useful for delayed oral galenic formulation of metformin.

21 Claims, 4 Drawing Sheets

ORAL PHARMACEUTICAL COMPOSITIONS WITH CONTROLLED RELEASE AND PROLONGED ABSORPTION

CROSS-REFERENCES TO RELATED APPLICATIONS

This application claims priority to U.S. application Ser. No. 10/332,463, filed Jan. 9, 2003, currently pending, which claims priority to PCT/FR01/02224, filed Jul. 10, 2001, which claims priority to FR 00 09047, filed Jul. 11, 2000. The contents of which are incorporated herein in their entirety.

The present invention relates to the technical field of pharmaceutical dosage systems with prolonged and controlled release of medicinal and/or nutritional active principles (AP), intended for oral administration.

More specifically, the invention is targeted at a pulverulent pharmaceutical composition which can be administered per os and which comprises at least one active principle AP absorbed in particular in the upper parts of the gastrointestinal tract and excipients capable of conferring thereon properties of prolonged absorption of the AP.

The oral route is the most convenient and the most widely used administration route for medicinal and/or dietary active principles. These systems have obvious advantages in terms of ease of administration and of tolerance for the patients.

It is particularly advantageous to seek to develop oral pharmaceutical dosage forms which provide therapeutic cover for the patient over a nychthemeron (24 hours). Such an objective is ambitious. This is because the majority of APs administered per os are absorbed in the upper part of the gastrointestinal tract, which constitutes a "window of absorption". The duration of passage of the AP through this window is limited in time. Consequently, the absorption time is itself limited. Thus, it is generally accepted that residence times for ingested oral forms are of the order of 0.5 to 3 hours approximately in the stomach and of 2 to 4 hours approximately in the small intestine, according to whether the subject has eaten nothing or whether the ingested oral forms are present in a sizeable food bolus. The duration of bioabsorption of an AP administered per os and for which the absorption is limited to the upper parts of the gastrointestinal tract (GIT) is therefore only a few hours.

An additional condition to that of increasing the bioabsorption time, which is the first objective of the pharmaceutical dosage system of the present invention, is that of maintaining the bioavailability of the AP at a satisfactory and sufficient level.

The combination of an increase in the bioabsorption time and the maintenance of the bioavailability at a satisfactory and sufficient level is an object which is difficult to achieve. A simple increase in the release time of the AP beyond the natural duration of the transit through the GIT generally results only in the release of a portion of the AP after the window of absorption and therefore in the lowering of the bioavailability of the AP.

In practice, the bioabsorption time (Tabs) is deduced from the plasma concentration profile (PCP) of the AP: this is the time at the end of which the PCP enters a situation of pure elimination.

The bioavailability is, for its part, evalued conventionally by the ratio of the area under the curve of the PCP to the area under the curve of the PCP of a reference immediate release form.

Numerous technical proposals have appeared in attempting to solve the problem set out above.

Taken as a whole, the prior technical proposals provide for an increase in the transit time of the AP by providing three types of pharmaceutical dosage systems, namely:
low-density floating systems, which float on the surface of the liquid gastric contents, thus prolonging the time during which the AP is present in the upper parts of the GIT;
bioadhesive systems, which adhere to the gastric and/or intestinal mucous membranes;
swelling systems, which increase in volume once they are in contact with the gastric fluids until dimensions are reached such that they cannot cross the pylorus and are thus retained in the stomach.

Some of the known systems can combine two or three of these flotation, bioadhesion and swelling functionalities.

Patent application PCT WO-99/47128 provides a review of the prior art relating to these three types of approach for the development of gastroretentive pharmaceutical dosage forms having properties of prolonged and controlled release of the AP.

This application PCT WO-99/47128 provides an oral pharmaceutical dosage form suitable for active principles having high solubility in water and exhibiting a window of absorption limited to the upper part of the gastrointestinal tract (metformin). For these highly soluble APs, this pharmaceutical dosage form claims to solve the problem consisting in simultaneously providing:
i) prolonged release without an initial "burst", and
ii) a prolonged gastric residence time.

This pharmaceutical dosage system with controlled release of AP has two phases. It comprises:
a particulate internal phase formed of individual granules charged with AP. The distinctive feature of these granules is that of being uncoated and of comprising one or more excipients which can be:
a hydrophobic polymer: copolymer of (meth)acrylic acid (Eudragit®), ethylcellulose,
and/or a hydrophilic polymer: sodium carboxymethylcellulose or sodium alginate,
and/or other hydrophobic compounds: waxes, fatty alcohols, fatty acid esters,
and a solid continuous external phase in which the particles of the internal phase are embedded, this solid continuous external phase comprising:
one or more hydrophilic polymers: [hydroxypropylmethylcellulose (HPMC) (with a viscosity of 5 cPs and $1 \times 10^5$ cPs), microcrystalline cellulose),
and/or one or more hydrophobic polymers,
and/or one or more other hydrophobic compounds (waxes, fatty alcohols, fatty acid esters).

This pharmaceutical dosage system is preferably in the tablet form. It is presented as having an increased residence time in the upper part of the gastrointestinal tract (stomach/small intestine) by an effect of increase in size, without, however, reaching an upper limit leading to blockage.

One disadvantage of this pharmaceutical dosage form is that it exhibits a variable gastric residence time, unlike a microparticulate pharmaceutical dosage form, the residence time of which is kept in balance by the large number of particles.

Furthermore, it is probable that this pharmaceutical dosage system according to WO-99/47128 (preferably a tablet) has a low mechanical strength in a gastric medium. Under such an assumption, the release of the AP would no longer be controlled.

Patent application PCT WO-99/47125 provides a pharmaceutical dosage form, the application of which is limited to antihyperglycemics of very high solubility and more particularly metformin. This form makes it possible to obtain therapeutic cover over 24 hours after oral administration in the nourished state. It is composed of a macroscopic tablet surrounded by a membrane which is permeable to water but not to the AP. The core of the invention is the development of a tablet which releases the AP by an osmotic effect. The release of the AP is controlled by adjusting the osmotic pressure by addition of a polymer which increases the inflow of water and by adjusting the rate for departure of the AP by inserting an orifice in the semipermeable membrane. The bioavailability is maintained by adding an absorption promoter, such as a bile salt, to the tablet.

The main disadvantage is the presence of this absorption promoter, which can weaken the intestinal wall and can, on prolonged administration, have undesirable side effects.

Another disadvantage is that this "tablet" form exhibits a variable gastric residence time, unlike a microparticulate pharmaceutical dosage form, the residence time of which is kept in balance by the large number of particles.

U.S. Pat. No. 5,472,704 provides a controlled release system which maintains the bioavailability of the AP by increasing the residence time of the pharmaceutical dosage form passing through the window of absorption of the AP in the (GIT). This bioadhesive pharmaceutical dosage system is composed of a plurality of individual particles, the largest dimension of which is at most 2 500 microns, in practice 300-600 microns. Each particle can comprise a bioadhesive part formed of an acrylate copolymer and of hydroxypropylmethylcellulose (HPMC) and a noncontinuous part comprising coated AP granules (125-600 μm) in which the AP is combined with an excipient which is active with regard to the prolonged and controlled release of said AP, this excipient not having bioadhesive properties (castor oil and/or lactose and/or polyvinyl alcohol and/or a vegetable oil and/or a calcium hydrogenphosphate, and the like).

The bioadhesive part comprises, for example:
cellulose derivatives or a mixture of acrylic copolymer (Carbopol) and of HPMC,
hydrophobic agents, such as stearic acid salts, hydrogenated vegetable oils, polyethylene glycols, talc, and the like,
and disintegrating agents of the following types: polyvinylpyrrolidone, starch functionalized by methyl and sodium carboxylate groups, starch, alginic acid, calcium carboxymethylcellulose, guar gum, silica, sodium alginate, gelatin, pectin, and the like.

The coated AP granules with a diameter of 125-600 μm are mixed with the excipients intended to form the bioadhesive part. This mixture is subsequently formed into tablets, which are subsequently milled and sieved, so as to obtain a powder comprising granules with a size of 300-600 μm.

The targeted purpose of the pharmaceutical dosage system according to U.S. Pat. No. 5,472,704 is the development of a bioadhesive system. In point of fact, as taught in WO-99/47128 discussed above, bioadhesive systems have not demonstrated their ability to increase the residence time in the upper parts of the GIT. Consequently, there is nothing in this U.S. Pat. No. 5,472,704 which allows it to be supposed that the pharmaceutical dosage system is capable of increasing the bioabsorption time of the AP.

Another type of pharmaceutical dosage system is also known, composed of a multiplicity of particles or microcapsules each carrying AP coated with a layer of film coating based on ethylcellulose, on polyvinylpyrrolidone, on magnesium stearate and on castor oil, for example. Such a pharmaceutical dosage system is disclosed in application PCT WO-96/11675. These reservoir microcapsules benefit from their multiplicity, which benefit is a more uniform and reproducible gastric emptying time. Furthermore, their size, of between 50 and 1 000 μm, and the characteristics of their coating make it possible to increase their transit time in the small intestine (between 8 and 24 hours) and, consequently, to maintain the absorption of the AP throughout all or part of this residence time in the small intestine.

As will be demonstrated clearly hereinbelow, the multiparticulate pharmaceutical dosage system according to WO 96/11675 can be improved as regards the absorption time and the bioavailability of active principles having a high solubility in water and absorbed in the upper part of the GIT, such as, for example, metformin.

In such a state of the art, one of the essential objectives of the present invention is to provide a novel improved pharmaceutical dosage system for the oral administration of active principles APs, in particular of APs having a high solubility in water and absorbed in the upper part of the GIT, this system having to make it possible to obtain effective therapeutic cover over 24 hours.

Another essential objective of the invention is to provide a gastroretentive pharmaceutical dosage system for the oral administration of an AP having a high solubility in water and absorbed in the upper part of the GIT, this system exhibiting an increased bioabsorption time, while maintaining the bioavailability of the AP at a sufficient and satisfactory level.

Another essential objective of the invention is to provide an oral pharmaceutical dosage composition for the administration of an AP having a high solubility in water, the in vitro release profile for the AP of which has a sigmoidal shape.

Another essential objective of the invention is to provide an oral pharmaceutical dosage composition of one dose per 24 hours type which is effective therapeutically, which can be tolerated by the patient, which is economic, which is easy to manufacture and in which recourse has been had to a combination of conventional and harmless pharmaceutical excipients.

Another essential objective of the invention is to provide a pharmaceutical dosage system of the type of that mentioned above which is provided in the form of gelatin capsules.

Another essential objective of the invention is to provide for the use of the abovementioned oral pharmaceutical dosage system or composition for the preparation of a medicament, in particular of a medicament with an active principle which is very soluble in water and more particularly still with an AP which is an antidiabetic, such as metformin.

These objectives, among others, are achieved by the present invention, which relates, first of all, to the oral pharmaceutical composition comprising at least one active principle (AP) and excipients capable of conferring, on this composition, properties of controlled release and of prolonged absorption of the AP in the gastrointestinal tract, this composition being of the type of those comprising:
first, a plurality of individual and coated particles comprising AP and excipients,
and, secondly, a continuous external phase of excipients, in which phase is dispersed this plurality of individual and coated particles, characterized in that:
-a- it comprises two systems for the controlled release of the AP combined in series, namely: individual and coated particles, first, and the continuous external phase, secondly;
-b- the individual and coated particles of AP are microcapsules having the following characteristics:
i) their coating film has the composition below:
1—at least one film-forming polymer (P1) which is insoluble in the fluids of the tract, present in a proportion of 50 to 90% by weight, preferably 50 to 80% by weight, on a dry basis with respect to the total mass of the coating composition and composed of at least one water-insoluble cellulose derivative, ethylcellulose and/or cellulose acetate being particularly preferred;

2—at least one nitrogenous polymer (P2), present in a proportion of 2 to 25% by weight, preferably of 5 to 15% by weight, on a dry basis with respect to the total mass of the coating composition and composed of at least one polyacrylamide and/or one poly-N-vinylamide and/or one poly-N-vinyllactam, polyacrylamide and/or polyvinylpyrrolidone being particularly preferred;

3—at least one plasticizer, present in a proportion of 2 to 20% by weight, preferably of 4 to 15% by weight, on a dry basis with respect to the total mass of the coating composition and composed of at least one of the following compounds: glycerol esters, phthalates, citrates, sebacates, esters of cetyl alcohol, castor oil, salicylic acid and cutin, castor oil being particularly preferred;

4—and optionally at least one surface-active agent and/or lubricating agent, present in a proportion of 2 to 20% by weight, preferably of 4 to 15% by weight, on a dry basis with respect to the total mass of the coating composition and chosen from anionic surfactants, preferably alkali metal or alkaline earth metal salts of fatty acids, stearic and/or oleic acid being preferred, and/or from nonionic surfactants, preferably polyoxyethylenated sorbitan esters and/or polyoxyethylenated derivatives of castor oil, and/or from lubricating agents, such as stearates, preferably calcium, magnesium, aluminum or zinc stearate, or such as stearylfumarate, preferably sodium stearylfumarate, and/or glyceryl behenate; it being possible for said agent to comprise just one or a mixture of abovesaid products;

(ii) they have a particle size of between 50 and 1 000 microns, preferably between 100 and 750 microns and more preferably still between 200 and 500 microns;

-c- The continuous phase of functional excipients comprises:

(i) at least one polyelectrolytic hydrophilic polymer (PEP) capable of gelling and/or crosslinking, preferably an acrylic or cellulose polymer or a polysaccharide and more preferably still an alginate;

(ii) at least one neutral hydrophilic polymer (NP), preferably chosen from the group consisting of celluloses, more especially hydroxypropyl-methylcellulose (HPMC) or hydroxypropylcellulose (HPC) and their derivatives;

(iii) and optionally a gelling/crosslinking additive (ADD) for the PEP polymer, preferably a compound based on a cation with a valency $\geq 2$, preferably a calcium-based compound and more preferably still calcium acetate;

-d- the mixture formed from the individual particles according to -b- and from the continuous phase according to -c- above spontaneously forms, in the presence of water in a dissolution test D, a composite macroscopic solid comprising a continuous external phase in the gel form in which is included a noncontinuous internal phase formed from the individual and coated AP particles, this composite macroscopic solid being formed spontaneously in a time of less than 30 minutes and preferably of between 1 and 20 minutes.

In an entirely advantageous way, even before their discharge from the matrix, the microcapsules make possible the controlled release of the AP and its absorption in the upper part of the gastrointestinal tract.

Furthermore, without wishing to be committed to a theory, it may be imagined that, by virtue of its in situ initial mechanical strength, this pharmaceutical dosage system makes possible gradual release of the microparticles (microcapsules) of internal phase into the stomach, as the gelled matrix is eroded by the gastric fluids.

According to another characteristic of the invention, this composition exhibits an in vitro dissolution curve in a test D having a sigmoidal appearance defined in the following way:

there exists a point T on the dissolution curve, the tangent to which passes through the origin without cutting the curve and the abscissa t of which is such that:

$t_T \geq 1$ H

20% of the AP is released within a time $t \geq 1.5$ H.

This in vitro dissolution curve is given by a test D which is defined as follows:

A gelatin capsule comprising the oral pharmaceutical dosage composition in the powder form is stirred using a paddle at 100 revolutions/min in a simulated gastric medium at a temperature of 37° C. This simulated gastric medium, a volume of 1 liter of which is employed, initially has a pH=1.2. This medium comprises 0.034 mol/l of NaCl, 0.063 mol/l of HCl and 3.2 g/l of pepsin. The pH is gradually brought to 4.5 by addition, to the medium of pH=1.2, of $KH_2PO_4$ (12 g) and of 35% NaOH.

Examples of dissolution curves in accordance with the invention are represented in the appended FIGS. 1 and 2.

It will be noted that the dissolution curves for the AP present in the pharmaceutical dosage systems according to the invention comprise a point T, the tangent to which passes through the origin and the abscissa $t_T$ of which is $\geq 1$ H, preferably $t_T \geq 1.5$ H and more preferably still is: $1 \leq t_T \leq 3$ H.

In other words, this means that the dissolution curves, in the test D, of the compositions according to the invention exhibit a first part in which the release of the AP is initially slow and for which the concavity is directed upward, followed by a part for which the concavity is directed downward.

The pharmaceutical dosage composition according to the invention makes it possible to increase the therapeutic cover of the AP by an increase in the $t_{max}$, while maintaining the bioavailability at a sufficient and satisfactory level. The curves giving the plasma concentrations of AP as a function of the time following ingestion of the composition, respectively for an immediate release AP (metformin) and for this same AP in a pharmaceutical dosage composition according to the invention, are shown in FIG. 3. The increase in the $t_{max}$ obtained by virtue of the formulation according to the invention is obvious.

According to a preferred characteristic of the invention, the composition of the coating film of the individual AP particles is as follows:

1—60 to 80% weight of P1=ethylcellulose
2—5 to 10% weight of P2=PVP
3—5 to 10% weight of plasticizer=castor oil
4—2 to 8% weight of lubricant/surfactant=magnesium stearate As regards the continuous external phase or matrix, it is preferable for its composition to be as follows:

i—60 to 90% by weight, preferably from 70 to 90% by weight, of gelling/crosslinking polyelectrolytic hydrophilic polymer (PEP), advantageously of alginate;

ii—5 to 40% by weight, preferably from 10 to 30% by weight, of neutral hydrophilic cellulose polymer (NP), advantageously of HPMC;

iii—1 to 5 by weight, preferably from 2 to 4% by weight, of a gelling/crosslinking additive (ADD), advantageously calcium acetate.

The viscosity $\eta$ may possibly be a criterion for selection of the PEP and NP polymers.

This viscosity $\eta$ is conventionally a viscosity measured at 25° C. for a polymer solution with an assay which can vary, for example: 1.25 or 2%. The methodology used is that set by the US pharmacopeia, namely USP 2208.

Thus, as regards the PEP polymer and more especially still sodium alginate, the products are selected which have a viscosity $\eta$ of:

between 300 and 1 000 mPa·s, preferably between 600 and 900 mPa·s. for a 1.25% solution in water.

As regards the neutral hydrophilic polymer NP, its viscosity $\eta$ is $\geq$10 000 mpa·s, preferably: 50 000 mpa·s$\leq\eta\leq$150 000 mpa·s, and more preferably still: 80 000 mpa·s$\leq\eta\leq$120 000 mpa·s for a 2% solution in water.

Mention may be made, as other examples of gelling polymers (PEP), of poly(acrylic acid)s, xanthan gums or carboxymethylcellulose.

HPMC is not the only neutral hydrophilic polymer (NP) capable of being suitable in the context of the invention. By way of alternative, hydroxypropyl-cellulose (HPC) might also be employed.

The gelling additives are specific to the polymers on which they exert their action. By way of illustration, barium, strontium, copper, nickel, zinc or manganese salts crosslink the alginate, resulting in the formation of a gel.

To continue with regard to weight considerations, it should be noted that the composition according to the invention has the advantageous characteristic of comprising:

from 50 to 80% by weight, preferably from 60 to 70% by weight, of continuous external phase, and 50 to 20% by weight, preferably from 40 to 30% by weight, of individual and coated particles of AP and of excipients.

Without this being limiting, the oral composition according to the invention is preferably pulverulent.

The oral composition according to the invention is a pulverulent form present in a gelatin capsule which, in an in vitro dissolution test D, spontaneously forms, in the presence of water, a cohesive solid formed from a gel matrix based on the continuous external phase and including the individual particles of AP coated with excipients. This cohesive solid is formed in less than 30 minutes and preferably between 1 and 20 minutes. It maintains its cohesion in the test D for at least 3 hours, thus providing, first, for the formation of an object with a size such that it cannot be expelled from the stomach during the time of the digestion during which the pylorus is in the closed position. However, during this phase, the AP is released into the system by virtue of the osmotic pressure exerted by the active principle.

After a few hours, the object disintegrates, thus releasing the microparticles, which can then migrate toward the small intestine, where they will continue to release the AP, thus increasing the absorption time for the AP in the body.

According to an alternative form, this pulverulent mixture could be formed into tablets capable of being converted in the gastrointestinal tract into a system comprising a gelled matrix based on the continuous external phase including the individual and coated particles of AP and of excipients.

As was seen above, the excipients selected and the way in which they are arranged in the pharmaceutical dosage system are essential characteristics of the invention. However, the functionalities of these excipients will be all the better expressed if the AP belongs to at least one of the following families of active substances:

antiulcer drugs, antidiabetics, anticoagulants, antithrombics, hypolipemics, antiarrhythmics, vasodilators, antianginals, antihypertensives, vasoprotectants, fertility promoters, uterine labor inducers and inhibitors, contraceptives, antibiotics, antifungals, antivirals, antineoplastics, anti-inflammatories, analgesics, antiepileptics, antiparkinsonians, neuroleptics, hypnotics, anxiolytics, psychostimulants, antimigraines, antidepressants, antitussives, antihistaminics or antiallergics;

this AP preferably being chosen from the following compounds:

metformin, pentoxyfylline, prazosin, diltiazem, ketoprofen, metoprolol, captopril, atenolol, salbutamol, ranitidine, quinidine, perindopril, morphine, verapamil and their mixtures.

The active principles to which the invention also relates could be nutritional and/or dietary supplements or their mixtures, such as, for example, vitamins, amino acids, antioxidants or trace elements, or their mixtures.

Vaccines can optionally constitute other medicinal APs.

At the quantitative level, the AP is present in a proportion of at least 10% by weight, preferably in a proportion of 15 to 50% by weight and more preferably still in a proportion of 20 to 40% by weight.

According to a preferred characteristic of the invention, the pharmaceutical dosage system to which it relates comprises the composition as defined above, this composition being present, preferably, in a gelatin capsule, for example made of gelatin, preferably in an amount of between 300 and 1 000 mg, and more preferably still between 400 and 700 mg.

According to another of its aspects, the invention relates to the use of the composition as defined above in the preparation of pharmaceutical or dietary forms which are preferably pulverulent and are present in gelatin capsules.

As regards the preparation of the oral pharmaceutical dosage composition according to the invention, it consists:

first, of the preparation of the noncontinuous internal phase of individual and coated particles of AP, and, secondly, of the preparation of a pulverulent mixture of excipients forming the continuous external phase, after hydration.

The two external and internal phases are subsequently mixed and optionally converted into tablets.

Naturally, the pharmaceutical dosage system according to the invention could comprise other nontoxic excipients used by a person skilled in the art in gelatin capsule and tablet forms. Preservatives, stabilizers, agents for combating adhesion and taste-masking agents can also be employed.

As regards the preparation of the discrete coated particles forming the internal phase, reference will be made to application PCT WO-96/11675, which is entirely incorporated in the present description by reference. More specifically, the coating of AP particle is carried out by spraying the coating composition onto the AP particles brought into motion, preferably by mechanical stirring or by fluidization.

As regards the continuous external phase, this is a matter of mixing powders, indeed even of mixing powders and solutions, and of drying by any means known to a person skilled in the art.

The examples which follow will make possible a better understanding of the invention and will make it possible to grasp all its advantages, and also the alternative embodiments which can be envisaged, without departing from the scope of the invention.

EXAMPLE 1

1.1—Products employed:
a—Active principle AP:
metformin/HCl, sold by Interchemical.
b—Excipient for coating the particles of internal phase:
Ethylcellulose, characterized by an ethoxyl level of between 48 and 49.5% and a viscosity of between 6 and 8 cP, manufactured by Dow and sold under the name Ethocel 7
Magnesium stearate, sold by Ackros
Polyvinylpyrrolidone, manufactured and sold by ISP under the name Plasdone K29/32
Castor oil, sold by Garbit Huileries.
c—Excipient in the external phase:
Sodium alginate, characterized by a viscosity of between 600 and 900 cP, sold by Monsanto under the name Keltone HVCR
Hydroxypropylmethylcellulose, characterized by a viscosity of between 80 000 and 120 000 cP, sold by Colorcon under the name Methocel K 100 M Premium EP
Calcium acetate, manufactured by Dr. Paul Lohman, USP23 powder grade.
d—Gelatin capsule:
green opaque gelatin capsules with a size of 00, manufactured and sold by Capsugel.

1.2—Methodology 1 kg of metformin·HCl, sieved between 200 and 500 μm, was film-coated in a fluidized air bed device (Niro, precision coater) with an 8% (w/w) acetone/isopropanol (60/40 (%) (w/w) solution composed of a mixture of ethocel 7, of plasdone K29/32, of castor oil and of magnesium stearate (example of composition and of amount of coating deposited in tables 1 and 2). These film-coated metformin particles were subsequently dry blended in a cube mixer with a mixture of sodium alginate powder, hydroxypropylmethylcellulose powder and calcium acetate powder. This mixture was finally introduced into gelatin capsules with a size of 00. The release of metformin·HCl was tested in vitro by the test D.

EXAMPLE 2

A gelatin capsule comprising 142.9 mg of metformin HCl is prepared; the level of coating deposited on the metformin·HCl microparticles is 26%.

Quantitative data are collated in table 1 below.

TABLE 1

| percentage composition of example 2 | | |
|---|---|---|
| Components | Percentage composition % (w/w) | Unit composition (mg) |
| Metformin•HCl | 25.47 | 142.9 mg |
| Ethocel 7 | 6.60 | 37.1 mg |
| Magnesium stearate | 0.89 | 5.0 mg |
| Castor oil | 0.72 | 4.0 mg |
| Plasdone K 29/32 | 0.72 | 4.0 mg |
| Kelton HVCR | 50.91 | 285.6 mg |
| Methocel premium K 100M | 13.12 | 73.6 mg |
| Calcium acetate | 1.57 | 8.8 mg |

Figure 1:
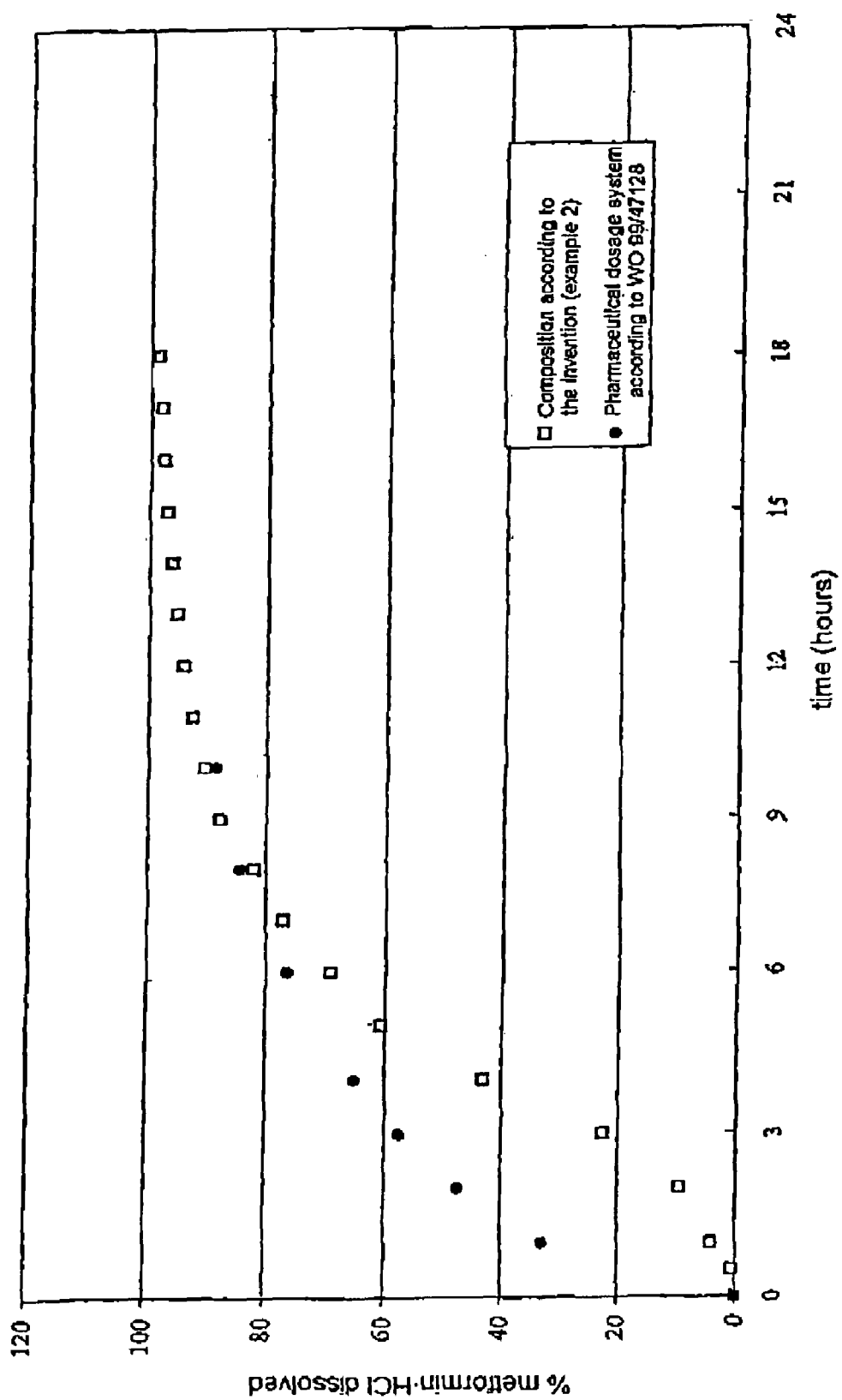
FIGS. 1 and 2 represent the dissolution profile for an AP (metformin), expressed by the % by weight of AP dissolved in the in vitro test D as a function of the time in hours, for the compositions of examples 2 and 3 respectively.

FIG. 1 shows the dissolution profile obtained. It is observed, with regard to this FIG. 1, that it comprises a point T, the tangent to which passes through the origin and the abscissa T of which is 5 H 20. Such a dissolution profile reveals a prolonged and controlled release of the AP. This also shows that the pharmaceutical dosage form according to the invention retains mechanical integrity (weight-dimension-cohesion) for a relatively long time (at least 4 h). The concavity of the first part of the curve (0-4 H) is directed upward: the release kinetics are slow and controlled.

This FIG. 1 also reveals the dissolution profile for the pharmaceutical dosage system according to application PCT WO-99/47128.

It is important to note the difference in appearance between the two curves, which corresponds to significant differences with respect to the in vivo behavior and thus to the absorption of the AP.

EXAMPLE 3

A gelatin capsule comprising 166.7 mg of metformin·HCl is prepared; the level of coating deposited on the metformin·HCl microparticles is 12%.

Quantitative data are presented in table 2 below.

TABLE 2

| percentage composition of example 3 | | |
|---|---|---|
| Components | Percentage composition % (w/w) | Unit composition (mg) |
| Metformin•HCl | 30.31 | 166.7 mg |
| Ethocel 7 | 3.06 | 16.8 mg |
| Magnesium stearate | 0.41 | 2.3 mg |
| Castor oil | 0.33 | 1.8 mg |
| Plasdone K 29/32 | 0.33 | 1.8 mg |
| Kelton HVCR | 50.87 | 279.8 mg |
| Methocel premium K 100M | 13.11 | 72.1 mg |
| Calcium acetate | 1.58 | 8.7 mg |

Figure 2:
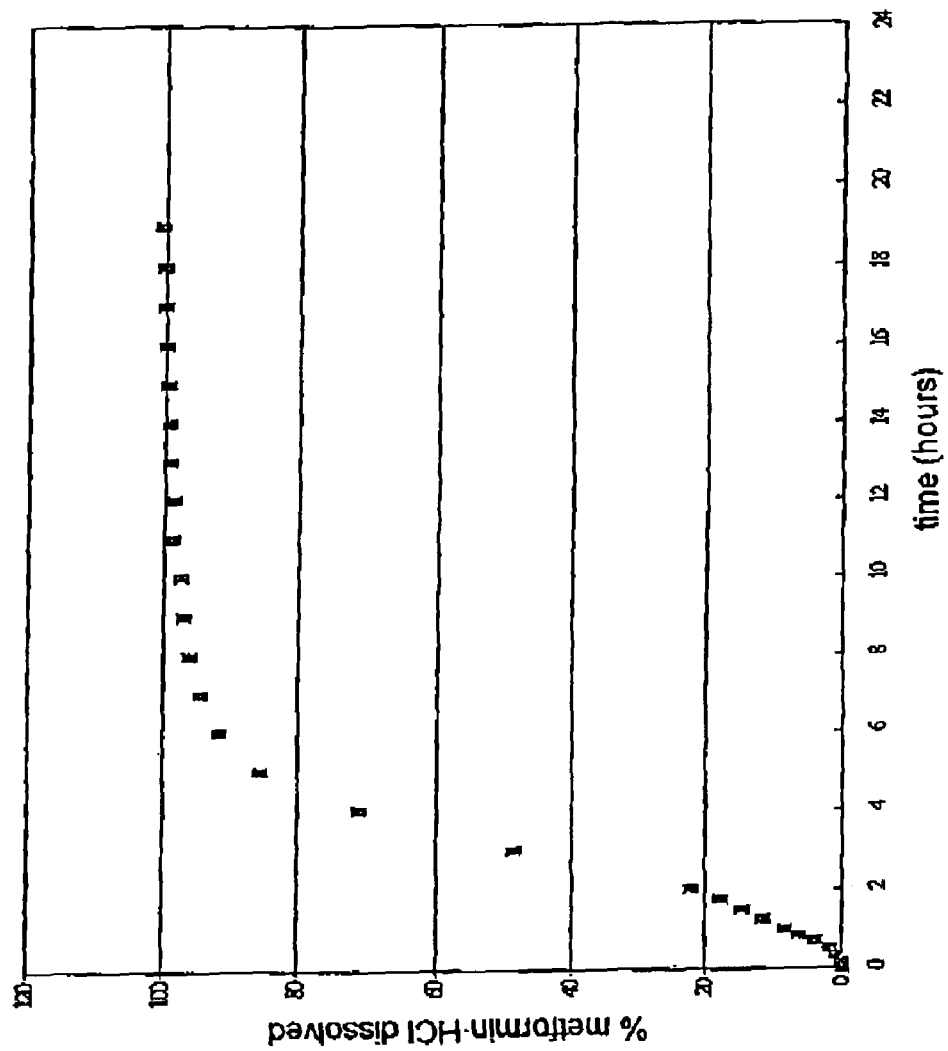

The appended FIG. 2 shows the dissolution profile obtained. Each point on this curve corresponds to a mean obtained with respect to 16 gelatin capsules. The curve in FIG. 2, corresponding to the composition according to the invention, comprises a point T, the tangent to which passes through the origin and the abscissa $t_T$ of which is 4 H.

Figure 2A:
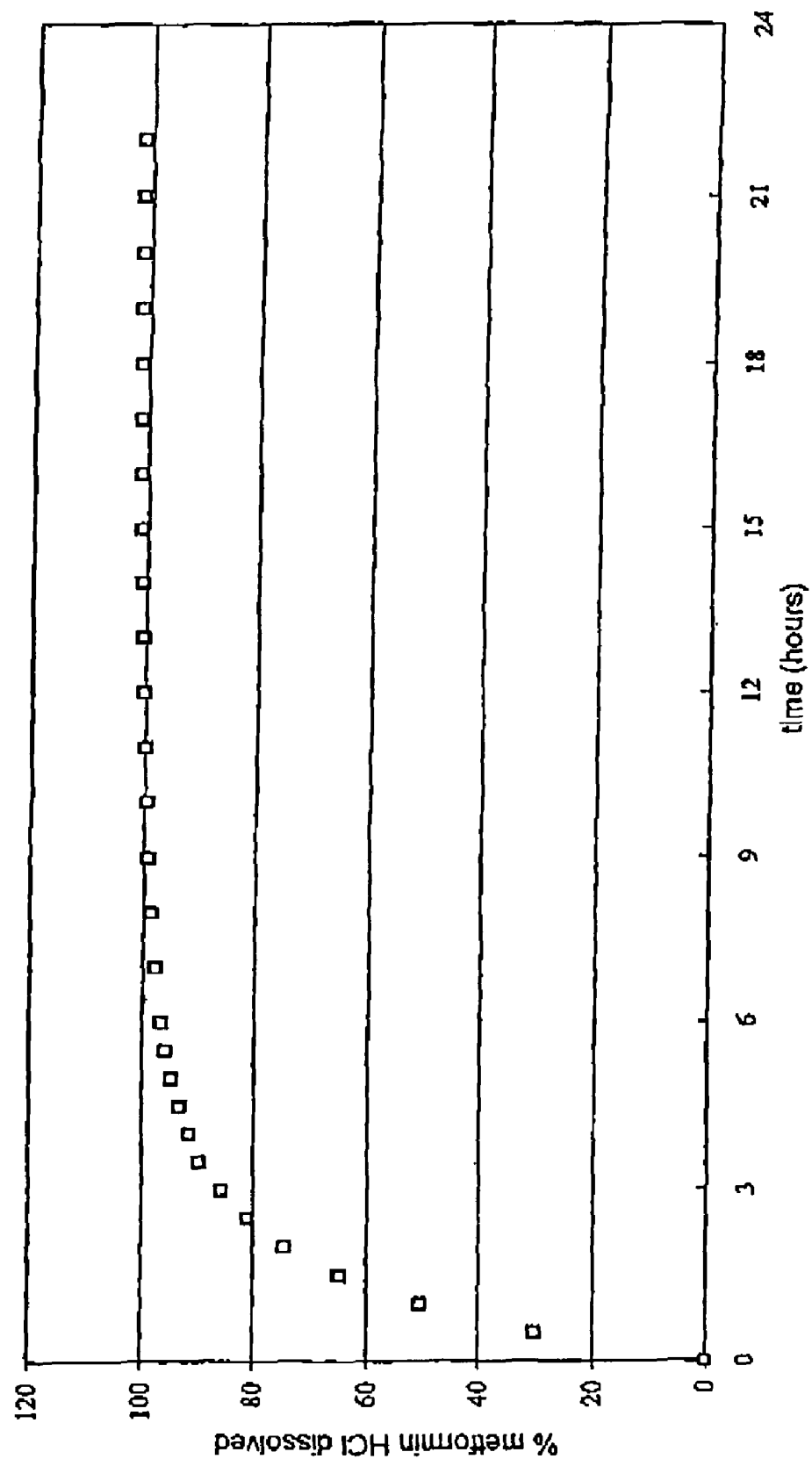
FIG. 2a represents the dissolution profile for an AP (metformin), expressed by the % by weight of AP dissolved in the in vitro test D as a function of the time in hours, for the microparticles according to WO 96/11675, taken by themselves alone and prepared according to the methodology described in point 1.2 of example 1.

The profile in FIG. 2 is of sigmoidal shape. It is clearly distinguished from the dissolution profile obtained with the coated microparticles alone (FIG. 2a) as obtained according to the methodology described in point 1.2 above of example 1. Comparison of FIGS. 2 and 2a also shows that the pharmaceutical dosage form according to the invention retains mechanical integrity (weight-dimension-cohesion) for a relatively long time (at least 4 H). The concavity of the first part of the curve (0-4 H) is directed upward.

EXAMPLE 4

Mechanical Strength in a Simulated Gastric Medium of the Composition According to the Invention Packaged in Gelatin Capsules Dissolution Conditions:

Dissolution at 37° C., stirring with a paddle at 100 revolutions/min, dissolution volume=1 liter.

pH=1.2: this medium is composed of 0.034 mol/l of NaCl and 0.063 mol/l of HCl with 3.2 g/l of pepsin.

pH=4.5: addition to the medium of pH=1.2 of $KH_2PO_4$ (12 g) and of 35% NaOH.

The gelatin capsules tested have the composition described in example 2 and are prepared according to the process described example 1.

Quantitative data are collated in table 3 below:

TABLE 3 quantitative data for mechanical strength with L the length of the gel cylinder, l the diameter of the gel cylinder and w the weight of the gel (gel ± internal water).

|  | L (mm) | l (mm) | w (mg) |
|---|---|---|---|
| 1 h at pH = 1.2 | 25.7 ± 0.5 | 10.7 ± 0.6 | 1 501 ± 68 |
| 2 h at pH = 4.5 | 27.7 ± 1.7 | 12 ± 1.4 | 2 478 ± 214 |
| 4 h at pH = 4.5 | 22.3 ± 1.7 | 12.3 ± 1.7 | 1 737 ± 229 |

It is apparent that, after 4 h in the medium with a pH of 4.5, L and l have not substantially varied. The gels formed, based on the pharmaceutical dosage composition according to the invention, have retained their integrity and their dimensions.

EXAMPLE 5

1 000 mg of metformin, distributed in 7 gelatin capsules with a size of 00 each comprising 561 mg of the pharmaceutical form according to the present invention, were administered to 6 healthy subjects after taking a meal. The plasma concentration of metformin is recorded as a function of the time between 0 and 36 hours after administration.

In this pharmaceutical form according to the invention, the metformin granules represent a fraction by weight of 25.5%, the coating of the granules a fraction by weight of 8.9% and, finally, the continuous external phase a fraction by weight of 65.6%.

The compositions are as follows:

| For the metformin granule: | | |
|---|---|---|
| Metformin | 100% | 142.9 mg |
| For the coating: | | |
| Ethocel 7 | 74% | 37.1 mg |
| Magnesium stearate | 10% | 5 mg |
| Plasdone K 29/32 | 8% | 4 mg |
| Castor oil | 8% | 4 mg |
| For the continuous phase: | | |
| Keltone HVCR | 77.6% | 285.6 mg |
| Methocel K 100M | 20.0% | 73.6 mg |
| Calcium acetate | 2.4% | 8.8 mg |

Figure 3:
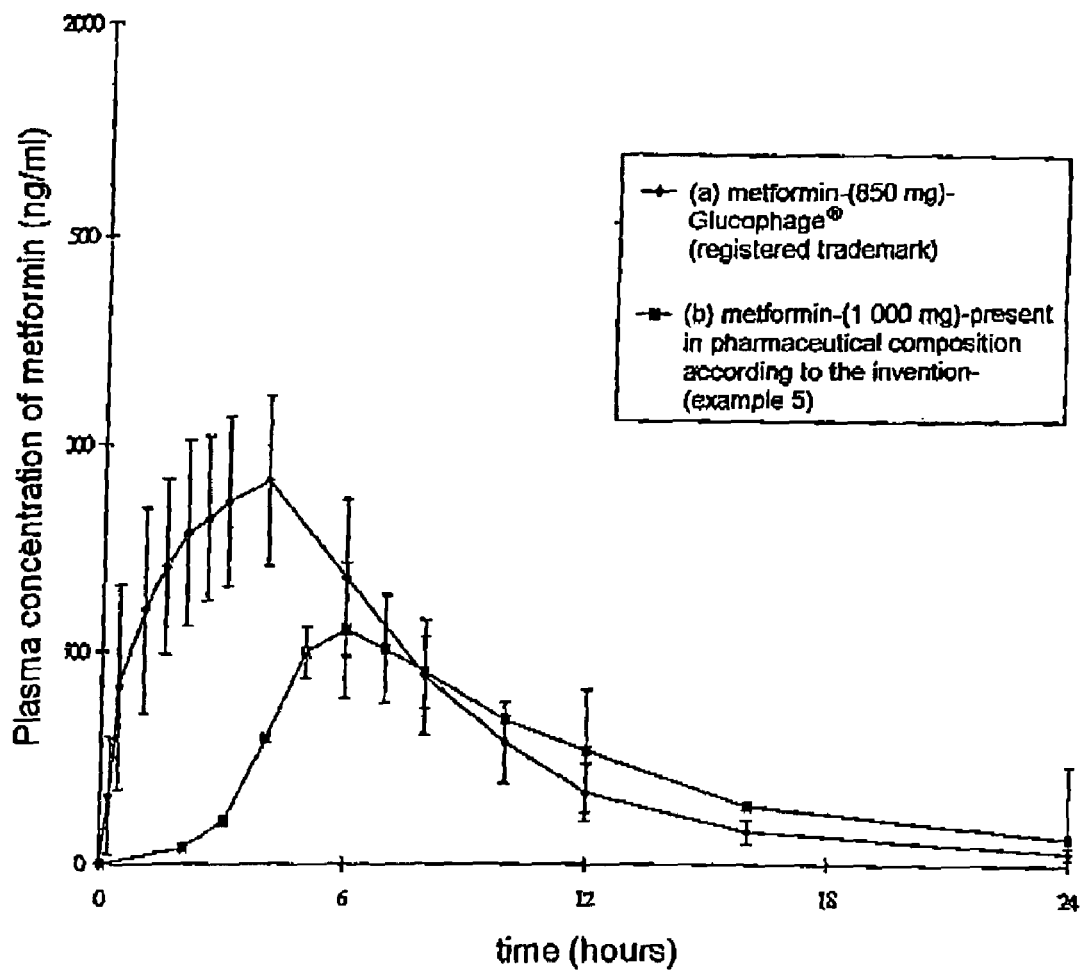
FIG. 3 represents the plasma concentration profiles of metformin after administration per os as a single dose to the subject:
(a): of 850 mg of metformin present in the Glucophage® immediate release form
(b): of 1 000 mg of metformin present in the pharmaceutical dosage form according to the present invention.
Reference should be made to example 5 for further details.

The mean plasma concentration profile with regard to 6 healthy subjects is represented in FIG. 3. For the purposes of comparison, the mean plasma concentration profile resulting from the administration to 24 healthy subjects, after a meal, of a single dose of 850 mg of the immediate release form of metformin, Glucophage®, is also displayed. These data result from the FDA (FOI) document: NDA 20-357, Metformin hydrochloride. Lipha Pharmaceutical Inc.

The pharmacokinetic data extracted from these profiles are listed in table 4 below:

TABLE 4 pharmacokinetic data

| Parameter | Formulation according to the invention | Glucophage ® |
|---|---|---|
| dose (mg) | 1 000 | 850 |
| Cmax (ng/ml) | 600 | 913 |
| T max (h) | 6 | 4 |
| AUC (ng · h/ml) | 5 233 | 7 980 |
| T absorption (h) | 10 | 4 |

It is thus clearly apparent that the pharmaceutical form according to the invention:

spectacularly increases the bioabsorption time, also increases the Tmax and maintains the AUC at more than 50% of the value corresponding to an immediate release oral form.

The invention claimed is:

1. An oral pharmaceutical composition for controlled release and prolonged absorption of at least one active principle in the gastrointestinal tract, wherein the composition comprises:

a plurality of particles having a diameter of 50 to 1000 microns, wherein the particles comprise at least one active principle and excipients, wherein the particles are individually coated with a coating composition; and wherein said coating composition comprises at least one film-forming polymer which is insoluble in the fluids of the intestinal tract, at least one nitrogenous polymer, and at least one plasticizer; and a continuous external phase of excipients comprising:

a polyelectrolytic hydrophilic polymer selected from the group consisting of polyelectrolytic acrylic polymers, polyelectrolytic cellulose polymers, polyelectrolytic polysaccharides polymers, and mixtures thereof, wherein the polyelectrolytic hydrophilic polymer is capable of gelling or crosslinking and is present in a proportion of 60 to 90% by weight on a dry basis with respect to the total mass of the continuous external phase;

a neutral hydrophilic polymer selected from the group consisting of hydroxypropylmethylcellulose (HPMC), hydroxypropylcellulose (HPC), and mixtures thereof, and wherein the neutral hydophilic polymer is present in a proportion of 5 to 40% by weight on a dry basis with respect to the total mass of the continuous external phase; and a gelling or crosslinking additive having a cation with a valency of two or more present in the proportion of 1 to 5% by weight on a dry basis with respect to the total mass of the continuous external phase; and wherein a mixture of said plurality of particles and of said continuous external phase of excipients spontaneously forms, in the presence of water in a dissolution test, a macroscopic solid gel composite in less than 30 minutes.

2. The oral pharmaceutical composition of claim 1, wherein said one film-forming polymer is present in a proportion of 50 to 90% by weight on a dry basis with respect to the total mass of the coating composition and is a non water soluble cellulose-based compound;

wherein said nitrogenous polymer is present in a proportion of 2 to 25% by weight on a dry basis with respect to the total mass of the coating composition and is selected from the group consisting of: polyacrylamide, poly-N-vinylamide, poly-N-vinyllactam, polyvinylpyrrolidone and mixtures thereof; and wherein said plasticizer is present in a proportion of 2 to 20% by weight on a dry basis with respect to the total mass of the coating composition and is selected from the group consisting of: glycerol esters, phthalates, citrates, sebacates, esters of cetyl alcohol, castor oil, and mixtures thereof.

3. The oral pharmaceutical composition of claim 2, wherein said film forming polymer is selected from the group consisting of: ethyl cellulose, cellulose acetate, and mixtures thereof.

4. The oral pharmaceutical composition of claim 2, wherein said coating composition further comprises at least one surface-active or lubricating agent that is present in a proportion of 2 to 20% by weight on a dry basis with respect to the total mass of the coating composition.

5. The oral pharmaceutical composition of claim 4, wherein said surface-active or lubricating agent selected from the group consisting of: anionic surfactants, alkali metals, alkaline earth metal salts of fatty acids, nonionic surfactants, polyoxyethylenated sorbitan esters, polyoxyethylenated castor oil-based compounds, stearates, stearic acid, oleic acid, calcium stearate, aluminium stearate, zinc stearate, stearylfumarates, and mixtures thereof.

6. The oral pharmaceutical composition of claim 2, wherein the film-forming polymer is ethylcellulose and is present in a proportion of 50 to 80% by weight on a dry basis with respect to the total mass of the coating composition, wherein the nitrogenous polymer is polyvinylpyrrolidone and is present in a proportion of 5 to 15% by weight on a dry basis with respect to the total mass of the coating composition, wherein the plasticizer is castor oil and is present in a proportion of 4 to 15% by weight on a dry basis with respect to the total mass of the coating composition, and wherein the surface-active or lubricating agent is magnesium stearate and is present in a proportion of 4 to 15% by weight on a dry basis with respect to the total mass of the coating composition.

7. The oral pharmaceutical composition of claim 1, wherein said gelling or crosslinking additive is a calcium based compound.

8. The oral pharmaceutical composition of claim 7, wherein said gelling or crosslinking additive is calcium acetate.

9. The oral pharmaceutical composition of claim 1, wherein the at least one polyelectrolytic hydrophilic polymer is alginate, wherein the at least one neutral hydrophilic polymer is HPMC, and wherein the gelling or crosslinking additive is calcium acetate.

10. The oral pharmaceutical composition of claim 1, wherein the at least one polyelectrolytic hydrophilic polymer capable of gelling or crosslinking is alginate and is present in a proportion of 70 to 90% by weight on a dry basis with respect to the total mass of the continuous external phase; wherein the at least one neutral hydrophilic polymer is HPMC and is present in a proportion of 10 to 30% by weight on a dry basis with respect to the total mass of the continuous external phase; and wherein the gelling or crosslinking additive is calcium acetate and is present in a proportion of 2 to 4% by weight on a dry basis with respect to the total mass of the continuous external phase.

11. The oral pharmaceutical composition of claim 1, wherein said composition exhibits an in vitro dissolution curve in a dissolution test such that the time to release 20% of the active principle is greater than or equal to 1.5 hours and such that the dissolution curve has a sigmoidal appearance where the point on the dissolution curve where the tangent passes through the origin without cutting the curve has an abscissa greater than or equal to one hour.

12. The oral pharmaceutical composition of claim 1, wherein the at least one neutral hydrophilic polymer has a viscosity η at 25° C. of 10,000 or more mPas at a concentration of 2% and according to the conditions set by US pharmacopeia 2208.

13. The oral pharmaceutical composition of claim 1, wherein the continuous external phase is present in a proportion from 50% to 80% by weight on a dry basis with respect to the total mass of the composition, and wherein the plurality of particles are present in a proportion from 20 to 50% by weight on a dry basis with respect to the total mass of the composition.

14. The oral pharmaceutical composition of claim 1, wherein the composition is in a pulverulent form and the spontaneous formation of a continuous external phase of excipients occurs after the composition is orally ingested.

15. The oral pharmaceutical composition of claim 14, wherein the pulverulent composition is present in a gelatin capsule, and wherein the continuous external phase and plurality of particles spontaneously forms a cohesive solid in the presence of water that maintains its cohesion in an in vitro dissolution test for at least 3 hours.

16. The oral pharmaceutical composition of claim 1, wherein the continuous external phase and plurality of particles are present in a tablet form such that when the tablet is orally ingested, the continuous external phase and plurality of particles spontaneously forms a cohesive solid.

17. The oral pharmaceutical composition of claim 1, wherein the active principle is selected from the group consisting of: antiulcer drugs, antidiabetics, anticoagulants, antithrombics, hypolipemics, antiarrhythmics, vasodilators, antianginals, antihypertensives, vasoprotectants, fertility promoters, uterine labor inducers and inhibitors, contraceptives, antibiotics, antifungals, antivirals, antineoplastics, antiinflammatories, analgesics, antiepileptics, antiparkinsonians, neuroleptics, hypnotics, anxiolytics, psychostimulants, antimigraines, antidepressants, antitussives, antihistaminics, antiallergics, metformin, pentoxyfylline, prazosin, diltiazem, ketoprofen, metoprolol, captopril, atenolol, salbutamol, ranitidine, quinidine, perindopril, morphine, verapamil and mixtures thereof.

18. The oral pharmaceutical composition of claim 1, wherein the active principle is present in a proportion of at most 40% by weight on a dry basis with respect to the total mass of the plurality of particles.

19. The oral pharmaceutical composition of claim 1, wherein the coating composition further comprises:
   2 to 20% of a surface-active or lubricating agent selected from the group consisting of: anionic surfactants, alkali metals, alkaline earth metal salts of fatty acids, nonionic surfactants, polyoxyethylenated sorbitan esters, polyoxyethylenated castor oil, stearates, stearic acid, oleic acid, calcium stearate, aluminium stearate, zinc stearate, stearylfumarates, and mixtures thereof.

20. The oral pharmaceutical composition of claim 1, wherein the coating composition further comprises the following compounds by weight on a dry basis with respect to the total mass of the coating composition:
   50-80% ethylcellulose, as film-forming polymer,
   5-15% polyvinylpyrrolidone, as nitrogenous polymer,
   4-15% castor oil, as plasticizer, and
   4-15% magnesium stearate, as lubricating agent;
   wherein the continuous external phase comprises the following compounds by weight on a dry basis with respect to the total mass of the continuous external phase:
   60-90% alginate, as polyelectrolytic hydrophilic polymer,
   20-50% HPMC, as neutral hydrophilic polymer, and
   2-4% calcium acetate.

21. The oral pharmaceutical composition of claim 1, wherein the at least one nitrogenous polymer is selected from the group consisting of poly-N-vinylamide or vinyllactam, and the at least one plasticizer is selected from the group consisting of glycerol esters and esters of cetyl alcohol.

* * * * *